US006499703B2

(12) United States Patent
Chou

(10) Patent No.: US 6,499,703 B2
(45) Date of Patent: Dec. 31, 2002

(54) COMPUTER WRIST PAD ADJUSTABLE IN HEIGHT AND HARDNESS

(76) Inventor: Chien-Fa Chou, 3F, No. 23, Alley 2, Lane 87, Tien Mu N. Rd., Shih Lin Zone, Taipei (TW)

( * ) Notice: Subject to any disclaimer, the term of this patent is extended or adjusted under 35 U.S.C. 154(b) by 0 days.

(21) Appl. No.: 09/767,699

(22) Filed: Jan. 24, 2001

(65) Prior Publication Data

US 2001/0009263 A1 Jul. 26, 2001

(30) Foreign Application Priority Data

Jan. 26, 2000 (TW) ..................................... 89201371 U

(51) Int. Cl.$^{7}$ .......................... B68G 5/00; B43L 15/00; A61F 5/00

(52) U.S. Cl. .................... 248/118; 248/118.3; 248/918; 248/118.1

(58) Field of Search .......................... 248/118.1, 118.3, 248/918; 400/715, 717, 718

(56) References Cited

U.S. PATENT DOCUMENTS 5,121,962 A * 6/1992 Weber et al. ............... 297/214
5,125,606 A * 6/1992 Cassano et al. ............. 248/118
5,374,018 A * 12/1994 Daneshvar .................. 248/118
5,566,913 A * 10/1996 Prokop ....................... 248/118
5,568,907 A * 10/1996 Wolfe et al. ................ 248/118
5,601,264 A * 2/1997 Peart ....................... 248/118.1
5,713,544 A * 2/1998 Wolf et al. ................. 248/118
5,980,143 A * 11/1999 Bayer et al. ................ 400/715
6,133,556 A * 10/2000 Ramsey et al. ............. 219/521
6,195,255 B1 * 1/2001 Kim .......................... 361/683
6,182,316 B1 * 2/2001 Thomas et al. ................ 5/722
6,219,867 B1 * 4/2001 Yates ......................... 5/655.5

* cited by examiner

*Primary Examiner*—Korie Chan
*Assistant Examiner*—Deborah M. Brann
(74) *Attorney, Agent, or Firm*—Browdy and Neimark, P.L.L.C.

(57) ABSTRACT

A computer wrist pad having a bottom seat, an outer layer, two end plates, and at least one air sac. The bottom seat is provided with an open-ended receiving space in which the air sac is disposed. The receiving space is sealed off at both ends thereof by the two end plates. The air sac is inflatable and deflatable for adjusting the hardness and the thickness of the computer wrist pad.

9 Claims, 6 Drawing Sheets

COMPUTER WRIST PAD ADJUSTABLE IN HEIGHT AND HARDNESS

FIELD OF THE INVENTION

The present invention relates generally to a computer peripheral equipment, and more particularly to a computer wrist pad which can be adjusted in height and hardness.

BACKGROUND OF THE INVENTION

The conventional computer wrist pad is made of ethylenevinylacetate (EVA) foam body which is attached to a piece of cloth. There are keyboard wrist pads and mouse wrist pads. The computer wrist pad is intended to soothe the wrist of a computer user. However, the conventional computer wrist pad has a fixed hardness and a fixed thickness, which provide little help in alleviating the pain or discomfort to the wrist of the computer user, in view of the fact that the operating motion of the computer is different from person to person, and that the arm weight differs from person to person.

SUMMARY OF THE INVENTION

The primary objective of the present invention is to provide a computer wrist pad with means to adjust the hardness and the thickness of the computer wrist pad.

The computer wrist pad comprises a bottom seat, a soft outer layer, at least one air sac, and two side plates. The bottom seat is provided with a receiving space, which is sealed off by the two side plates. The air sac is disposed in the receiving space and is provided with an inflation port which is located in one of the side plates. The thickness and the hardness of the computer wrist pad are adjusted by the extent to which the air sac is inflated.

DETAILED DESCRIPTION OF THE INVENTION

Figure 1:
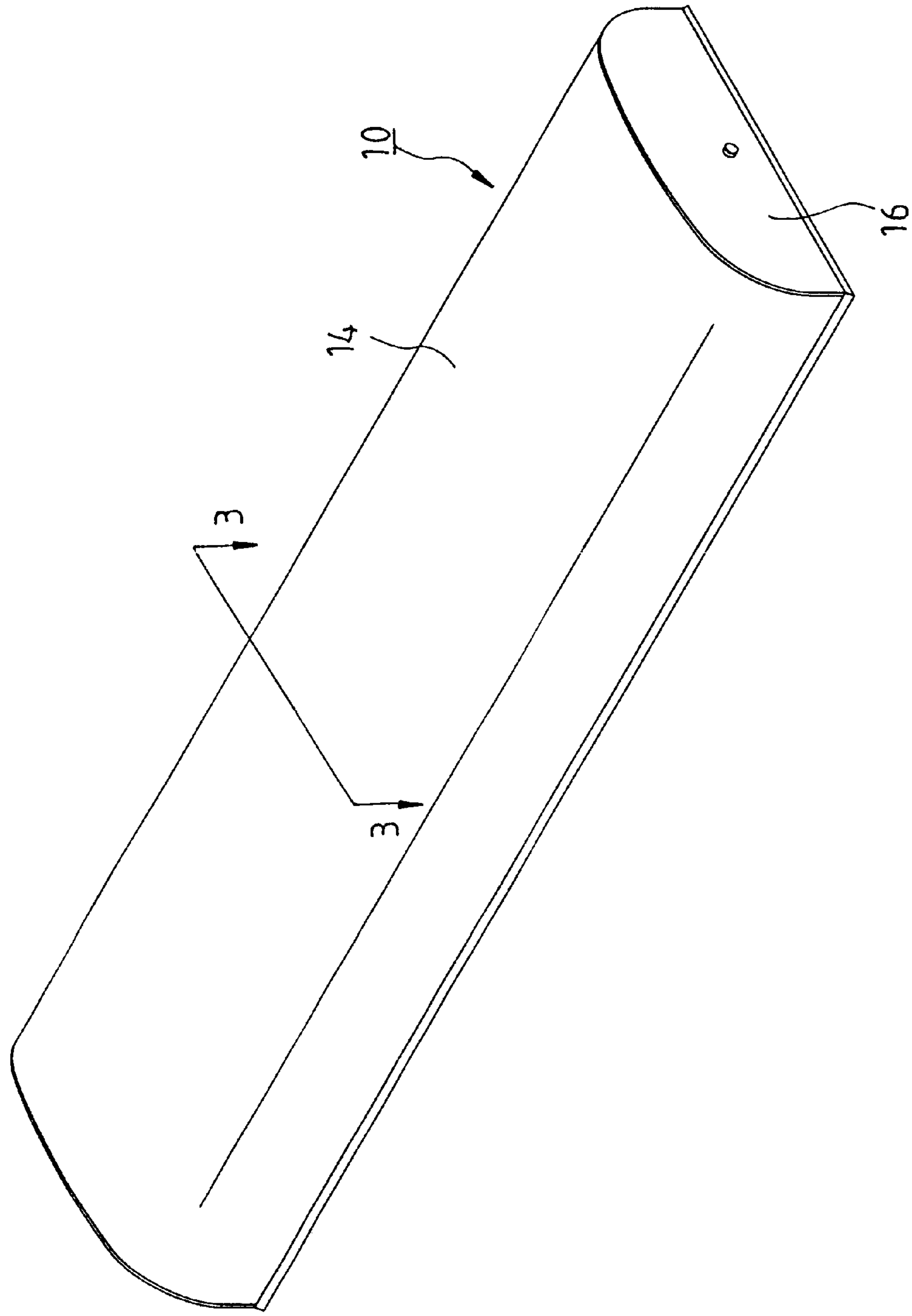
FIG. 1 shows a perspective view of a first preferred embodiment of the present invention.
Figure 2:
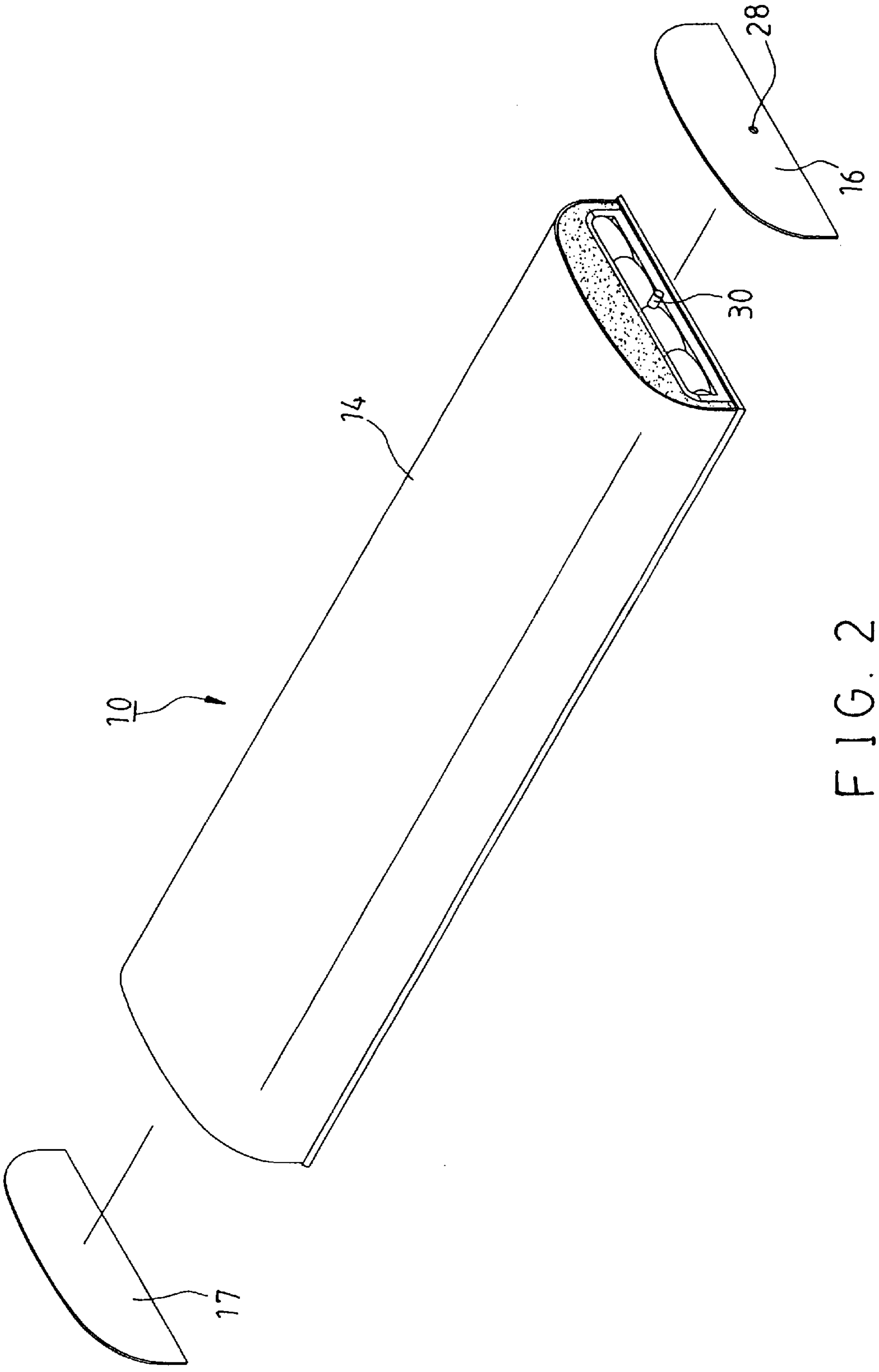
FIG. 2 shows a partial exploded view of the first preferred embodiment of the present invention.
Figure 3:
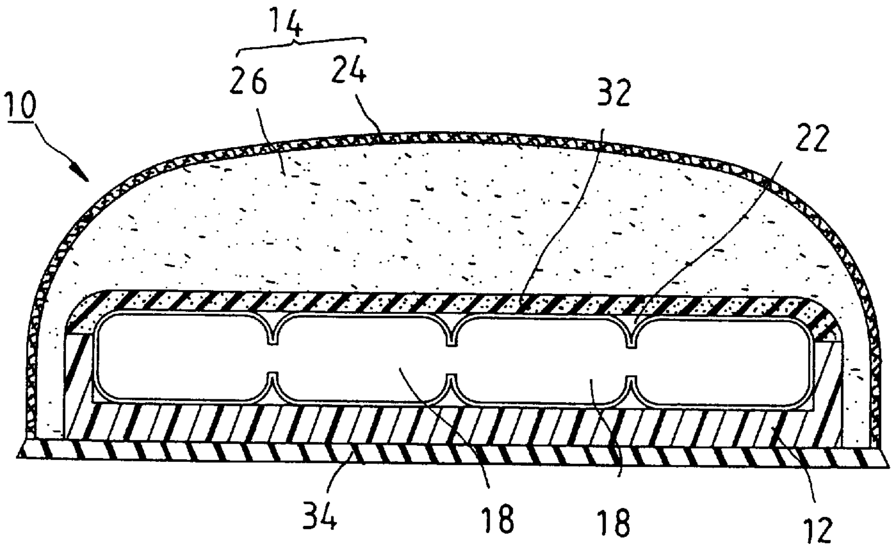
FIG. 3 shows a sectional view taken along the direction indicated by a line 3—3 as shown in FIG. 1.

As shown in FIGS. 1–3, a computer wrist pad 10 embodied in the present invention having a bottom seat 12, an outer layer 14, two side plates 16 and 17, and four air sacs 18 in communication with one another.

The bottom seat 12 has a U-shaped cross section and is made of a plastic material by injection molding or a metal material. The bottom seat 12 is provided with an open-ended receiving space 22.

The outer layer 14 is formed of an elastic cloth 24 and a polyurethane (PU) artificial sponge attached to the underside of the elastic cloth 24. The outer layer 14 covers the top of the bottom seat 12.

The two side plates 16 and 17 are disposed at the two ends of the bottom seat 12 for sealing off the receiving space 22. The first side plate 16 is provided with a receiving port 28.

The air sacs 18 are made of polyvinylchloride (PCV) or polyurethane (PU) and are disposed in the receiving space 22. The air sacs 18 are provided at one end with an inflation port 30 in communication with atmosphere air.

The computer wrist pad 10 further comprises a pressure diffusion layer 32, which is located between the outer layer 14 and the air sacs 18 and is made of ethylenevinylacetate (EVA), polyvinylchloride (PVC), polyethylene (PE), or polypropylene (PP). The pressure diffusion layer 32 is intended to transmit uniformly the pressure exerted on the top of the outer layer 14 to the air sacs 18. A skidproof layer 34 is disposed in the underside of the bottom seat 23 and is made of EVA, PE, PP or rubberlike material.

Figure 4:
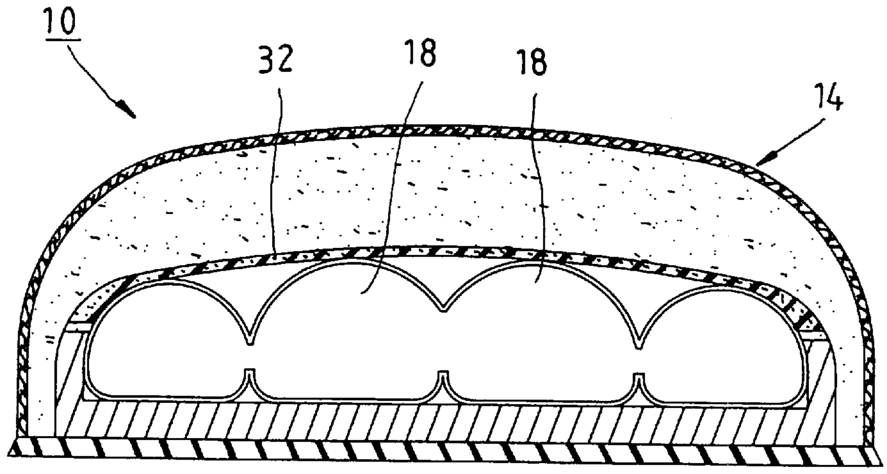
FIG. 4 shows a schematic view of an inflated air sac of the preferred embodiment of the present invention.
Figure 5:
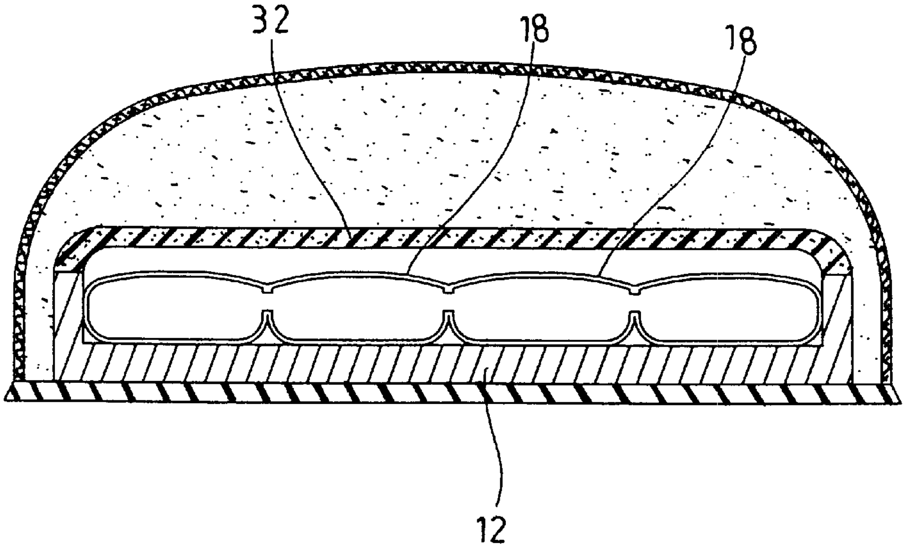
FIG. 5 shows a schematic view of the preferred embodiment of the present invention with the air sac being deflated.

The hardness and the thickness of the computer wrist pad 10 can be adjusted, as shown in FIG. 4, by inflating the air sacs 18 to result in an increase in hardness and thickness. Alternately, the air sacs 18 can be appropriately deflated to result in a decrease in hardness and thickness of the pad 10, as shown in FIG. 5.

Figure 6:
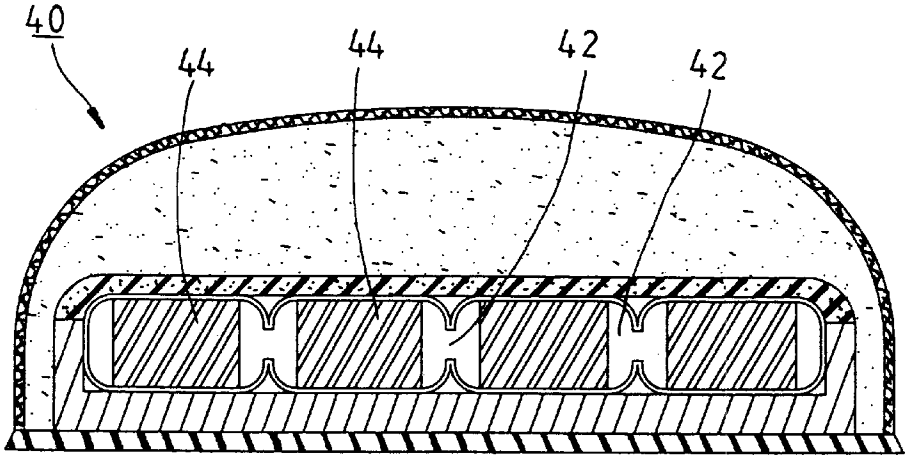
FIG. 6 shows a sectional view of air sac and elastomer of a second preferred embodiment of the present invention.

As shown in FIG. 6, a computer wrist pad 40 of the second preferred embodiment of the present invention is basically similar in construction to the computer wrist pad 10 described above, except that the former comprises air sacs 42 which are provided with an elastomer 44 of EVA, PVC, PE, PP, or rubberlike material. The elastomers 44 serve to support the wrist at the time when the air sacs 42 are not inflated.

Figure 7:
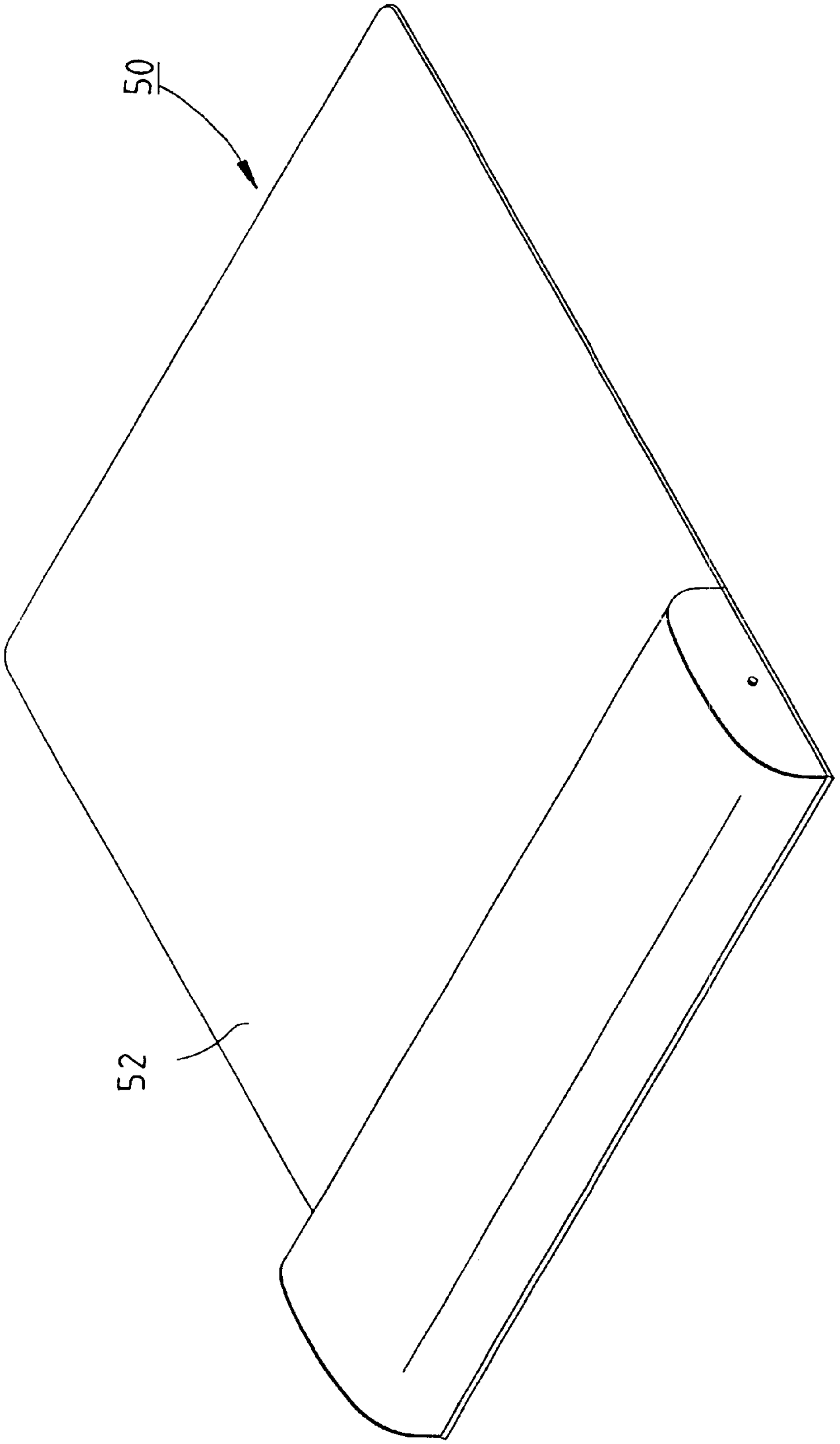
FIG. 7 shows a perspective view of a third preferred embodiment of the present invention.

As shown in FIG. 7, a computer wrist pad 50 of the third preferred embodiment of the present invention is provided with a platelike pad body 52 which has a greater area and is attached to the underside of the bottom seat (not shown in the drawing).

Figure 8:
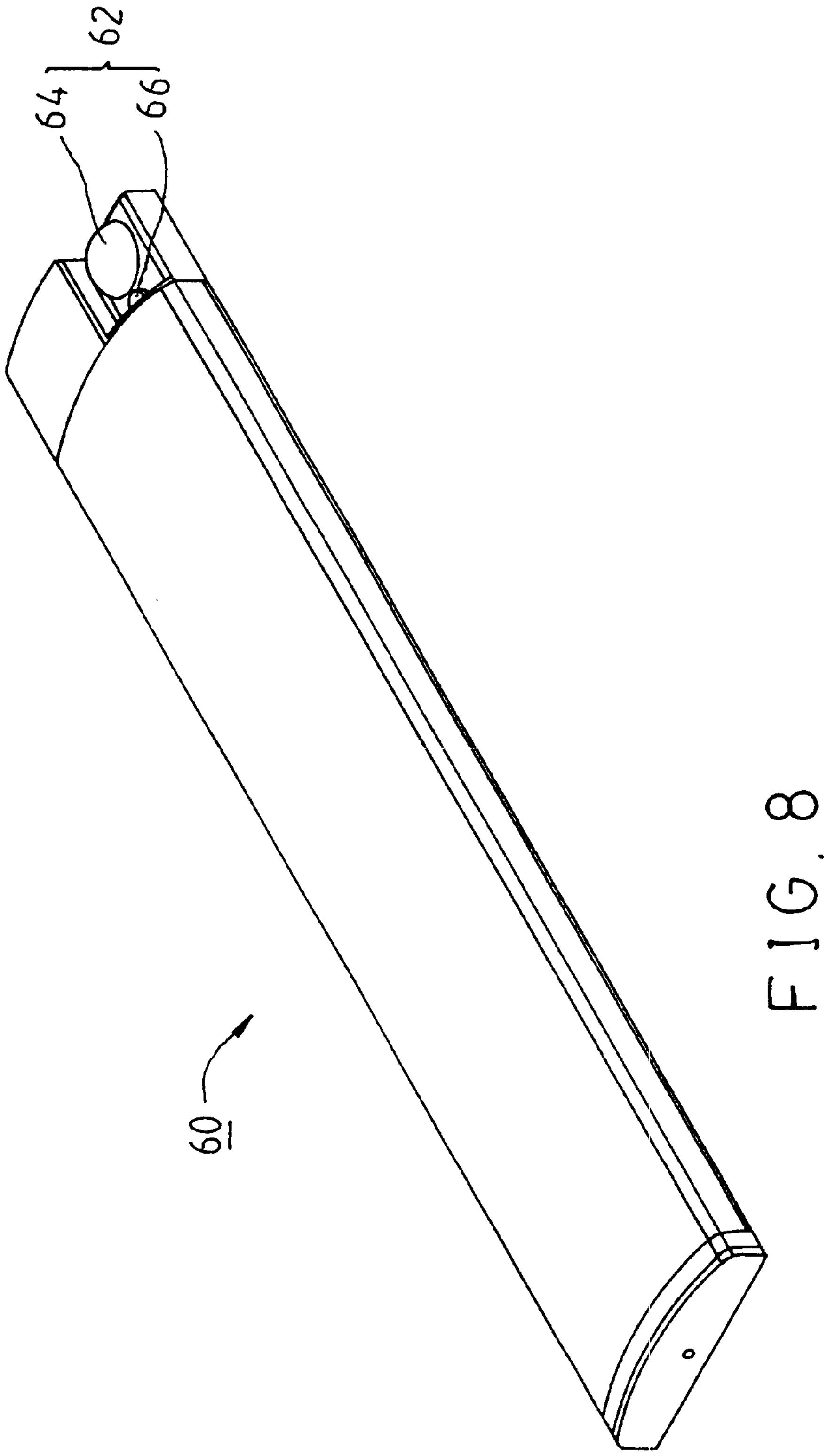
FIG. 8 shows a perspective view of a fourth preferred embodiment of the present invention.

As shown in FIG. 8, a computer wrist pad 60 of the fourth preferred embodiment of the present invention is basically similar in construction to the pad 10, except that the former comprises a prior art inflation-deflation device 62, which is in communication with the air sacs and is provided with an inflation ball sac 64 and a deflation valve 66.

What is claimed is:

1. A computer wrist pad comprising:

a bottom seat provided with an open-ended receiving space;

an outer layer having a softness and covering said bottom seat;

two side plates each respectively disposed at two ends of said bottom seat to seal off said receiving space;

at least one air sac which is inflatable and deflatable and is disposed in said receiving space from and between each of the two side plates and on a longitudinal center line of the wrist pad, said air sac having an inflation port located in one of said two side plates;

a pressure diffusion layer between said outer layer and said air sac, and wherein the air sac when inflated increases a hardness of the pad and a thickness between an underside of the bottom seat and a top side of the outer layer along the longitudinal center line of the wrist pad.

2. The computer wrist pad as defined in claim 1, wherein said pressure diffusion layer is made of a foam elastic body.

3. The computer wrist pad as defined in claim 1 further comprising a skidproof layer which is disposed on the underside of said bottom seat.

4. The computer wrist pad as defined in claim 3, wherein said skidproof layer is made of a rubber material.

5. The computer wrist pad as defined in claim 1 further comprising a pad body which is disposed in the underside of said bottom seat and is greater in area than said bottom seat.

6. The computer wrist pad as defined in claim 1, wherein said bottom seat is made of a plastic material.

7. The computer wrist pad as defined in claim 1, wherein said bottom seat is made of a metal material.

8. The computer wrist pad as defined in claim 1, wherein said outer layer is formed of an elastic cloth and an artificial sponge attached to the underside of said elastic cloth.

9. The computer wrist pad as defined in claim 1, wherein said air sac is provided with a plurality of elastomers contained therein.

* * * * *